United States Patent
Morschhäuser et al.

(10) Patent No.: US 7,151,137 B2
(45) Date of Patent: *Dec. 19, 2006

(54) ACRYLOYLDIMETHYLTAURINE ACID-BASED GRAFTED COPOLYMERS

(75) Inventors: Roman Morschhäuser, Mainz (DE); Matthias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/433,199

(22) PCT Filed: Nov. 28, 2001

(86) PCT No.: PCT/EP01/13857

§ 371 (c)(1),
(2), (4) Date: Nov. 10, 2003

(87) PCT Pub. No.: WO02/44269

PCT Pub. Date: Jun. 6, 2002

(65) Prior Publication Data

US 2004/0097657 A1    May 20, 2004

(30) Foreign Application Priority Data

Dec. 1, 2000   (DE) ................................ 100 59 832

(51) Int. Cl.
*C08F 12/30* (2006.01)
(52) U.S. Cl. ........................ 525/86; 525/158; 526/287; 526/288; 526/303.1; 526/307.2
(58) Field of Classification Search .................. 525/85, 525/158; 526/287, 288, 303.1, 307.2
See application file for complete search history.

(56) References Cited

U.S. PATENT DOCUMENTS

| 3,791,831 | A | * | 2/1974 | von Bonin et al. | ......... 430/529 |
|---|---|---|---|---|---|
| 3,931,089 | A | | 1/1976 | Karl | .................... 260/29.65 Q |
| 4,521,578 | A | | 6/1985 | Chen et al. | .................. 526/288 |
| 4,563,290 | A | * | 1/1986 | Okada et al. | ................ 507/226 |
| 5,075,401 | A | | 12/1991 | Zhang | ........................ 527/201 |
| 5,368,850 | A | | 11/1994 | Cauwet et al. | ................ 424/70 |
| 5,837,789 | A | | 11/1998 | Stockhausen et al. | |
| 5,879,718 | A | | 3/1999 | Sebillote-Arnaud | ......... 424/705 |
| 6,120,780 | A | | 9/2000 | Dupuis et al. | .............. 424/401 |
| 6,395,853 | B1 | | 5/2002 | Oswald et al. | |
| 6,468,549 | B1 | * | 10/2002 | Dupuis et al. | .............. 424/401 |
| 6,645,476 | B1 | | 11/2003 | Morschhaeuser | |

FOREIGN PATENT DOCUMENTS

| CA | 2363079 | 8/2000 |
|---|---|---|
| EP | 0 356 241 | 2/1990 |
| EP | 0 815 828 | 1/1998 |
| EP | 0 815 844 | 1/1998 |
| EP | 0 815 845 | 1/1998 |
| EP | 0 816 403 | 1/1998 |
| WO | WO 98/00094 | 1/1998 |

* cited by examiner

*Primary Examiner*—James J. Seidleck
*Assistant Examiner*—Olga Asinovsky
(74) *Attorney, Agent, or Firm*—Richard P. Silverman

(57) ABSTRACT

The invention provides water-soluble or water-swellable copolymers obtained by free-radical copolymerization of
A) acryloyldimethyltaurine and/or acryloyldimethyltaurates,
B) if desired, one or more other olefinically unsaturated, optionally crosslinking comonomers containing at least one oxygen, nitrogen, sulfur or phosphorus atom and possessing a molecular weight of less than 500 g/mol, the copolymerization
C) taking place in the presence of at least one polymeric additive having a number-average molecular weight of from 200 g/mol to $10^9$ g/mol.
The water-soluble or water-swellable copolymers of the present invention are useful in paper processing, laundry detergents, textile processing, petroleum extraction and formulating cosmetics.

6 Claims, No Drawings

ACRYLOYLDIMETHYLTAURINE ACID-BASED GRAFTED COPOLYMERS

The present invention relates to graft polymers based on acryloyldimethyltaurine and/or acryloyldimethyltaurates.

In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in petroleum extraction or as important base materials for cosmetics.

In the cosmetics sector a key role is assigned to polyelectrolytes. Besides water-soluble surface-active substances there is a high demand in this sector for systems which thicken oil and water. Thickeners of this kind, particularly the "superabsorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s.

In the 1990s, innovative thickeners based on acryloyldimethyltaurine (AMPS) and the salts thereof were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. Moreover, the microgel structure of such thickeners leads to a particularly pleasant skin sensation. The ease of processing and the favorable toxicological profile of the principal monomer imbue these thickeners with a high application potential. A disadvantage of acryloyldimethyltaurine-based thickeners is the frequent opalescence of their dilute aqueous gels. The cause of the opalescence is the high degree of scattering of visible light at overcrosslinked polymer fractions which arise during the polymerization and which in water are present only in an inadequately swollen form.

Surprisingly it has been found that grafted comb polymers based on acryloyldimethyltaurine (AMPS) which are obtainable by conducting the polymerization in the presence of a polymeric additive display the properties of a thickener in a very good manner, and a clear appearance.

The invention provides water-soluble or water-swellable copolymers obtainable by free-radical copolymerization of
A) acryloyldimethyltaurine and/or acryloyldimethyltaurates,
B) if desired, one or more other olefinically unsaturated, optionally crosslinking, comonomers containing at least one oxygen, nitrogen, sulfur or phosphorus atom and possessing a molecular weight of up to 500 g/mol, the copolymerization
C) taking place in the presence of at least one polymeric additive having number-average molecular weights of from 200 g/mol to $10^9$ g/mol.

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyldimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with a different degree of ethoxylation. It should be noted that the invention also embraces mixtures of two or more of the above-mentioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated monomers whose reaction parameters allow copolymerization with acryloyldimethyltaurine and/or acryloyldimethyltaurates in the respective reaction media.

Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4+$, monoalkylammonium, dialkylammonium, trialkylammonium and/or tetraalkylammonium radicals, in which the alkyl substituents of the amines independently of one another can be $(C_1-C_{22})$-alkyl radicals which may optionally be occupied by up to 3 $(C_2-C_{10})$-hydroxyalkyl groups. It is additionally possible to employ mono- to triethoxylated ammonium compounds with a different degree of ethoxylation. The degree of neutralization of the carboxylic acids can be between 0 and 100%.

Further preferred comonomers are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Essential to the invention is that the copolymerization is conducted in the presence of at least one polymeric additive C), the additive C) being added wholly or partly in solution to the polymerization medium before the actual copolymerization. The use of two or more additives C) is likewise in accordance with the invention. Crosslinked additives C) may likewise be used.

The additives C) or mixtures thereof must only be wholly or partly soluble in the chosen polymerization medium.

During the actual polymerization step the additive C) has a number of functions. On the one hand it prevents the formation of overcrosslinked polymer fractions in the copolymer which forms in the actual polymerization step, and on the other hand the additive C) is statistically attacked by active free radicals in accordance with the very well-known mechanism of graft copolymerization. Depending on the particular additive C), this results in greater or lesser fractions of the additive being incorporated into the copolymers. Moreover, suitable additives C) possess the property of altering the solution parameters of the copolymers which form during the free-radical polymerization reaction in such a way that the average molecular weights are shifted to higher values. As compared with analogous copolymers prepared without the addition of the additives C), those prepared with the addition of additives C) advantageously exhibit a significantly higher viscosity in aqueous solution.

Preferred additives C) are homopolymers and copolymers which are soluble in water and/or alcohols. The term "copolymers" also comprehends those having more than two different monomer types.

Particularly preferred additives C) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives C) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives C) is preferably from $10^2$ to $10^7$ g/mol, more preferably from $0.5*10^4$ to $10^6$ g/mol.

The amount in which the polymeric additive C) is used, based on the total mass of the monomers to be polymerized during the copolymerization, is preferably from 0.1 to 90% by weight, more preferably from 1 to 20% by weight, and with particular preference from 1.5 to 10% by weight.

In one further preferred embodiment the copolymers of the invention are crosslinked, i.e., they contain comonomers containing at least two polymerizable vinyl groups.

Preferred crosslinkers are methylenebisacrylamide; methylenebismethacrylamide; esters of unsaturated monocarboxylic and polycarboxylic acids with polyols, preferably di-acrylates and tri-acrylates and -methacrylates, more preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA).

Based on the total mass of the copolymers, the weight fraction of crosslinking comonomers is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction can be conducted, for example, as a precipitation polymerization, emulsion polymerization, bulk polymerization, solution polymerization or gel polymerization. Particularly advantageous for the profile of properties of the copolymers of the invention is precipitation polymerization, preferably in tert-butanol.

The polyfunctional polymers of the invention possess a great stuctural diversity and, consequently, broad potential possibilities for use, which can be tailored to virtually any task where interface effects and/or surface effects have a part to play. Attention is drawn in particular to the possibilities for application in the field of cosmetology, as thickeners for example. The term "custom-tailored polymers" gives a vivid description of the possibilities which this new class of polymer provides to the user.

Examples below are intended to illustrate the invention without, however, restricting it to them.

EXAMPLE 1

| Reactants | amount (g) |
| --- | --- |
| $NH_3$-neutralized AMPS | 80 |
| t-Butanol | 300 |
| TMPTA | 1.8 |
| Dilauroyl peroxide (initiator) | 1 |
| Poly-N-vinylpyrrolidone (® K-15, BASF) | 5 |

The polymer was prepared by the precipitation method in tert-butanol. The monomers in t-butanol were introduced as an initial charge and the reaction mixture was rendered inert, and then, after initial heating, the reaction was initiated by addition of DLP. The polymer was isolated by removing the solvent under suction and by subsequent vacuum drying.

EXAMPLE 2

| Reactants | amount (g) |
| --- | --- |
| $NH_3$-neutralized AMPS | 80 |
| N-Vinylpyrrolidone | 5 |
| Water | 300 |
| AMA | 0.9 |
| $Na_2S_2O_8$ (initiator) | 1 |
| Poly-N-vinylpyrrolidone (® K-30, BASF) | 10 |

The polymer was prepared by the gel polymerization method in water. The monomers were dissolved in water, the reaction mixture was rendered inert, and then, after initial heating, the reaction was initiated by addition of sodium peroxodisulfate. The polymer gel was subsequently comminuted and the polymer was isolated by vacuum drying.

EXAMPLE 3

| Reactants | amount (g) |
| --- | --- |
| AMPS | 80 |
| Vinyl acetate | 20 |
| Cyclohexane | 200 |
| Water | 300 |
| ® Span 80 | 1 |
| $Na_2S_2O_8$ (initiator) | 1 |
| Poly[N-vinylpyrrolidone-co-acrylic acid] (30/70) | 4 |

The polymer was prepared by the emulsion method in water. The monomers were emulsified in water/cyclohexane using ®Span 80, the reaction mixture was rendered inert using $N_2$, and then, after initial heating, the reaction was initiated by addition of sodium peroxodisulfate. The polymer emulsion was subsequently evaporated down and by this means the polymer was isolated.

EXAMPLE 4

| Reactants | amount (g) |
| --- | --- |
| $NH_3$-neutralized AMPS | 80 |
| t-Butanol | 300 |
| N-Vinylformamide | 20 |
| TMPTA | 1.8 |
| ABAH (initiator) | 1 |
| Poly[N-vinylcaprolactone-co-acrylic acid] (10/90) | 10 |

The polymer was prepared by the precipitation method in tert-butanol. The monomers in t-butanol were introduced as an initial charge, the reaction mixture was rendered inert, and then, after initial heating, the reaction was initiated by addition of ABAH. The polymer was isolated by removal of the solvent under suction and by subsequent vacuum drying.

EXAMPLE 5

| Reactants | amount (g) |
| --- | --- |
| Na-neutralized AMPS | 80 |
| Water | 300 |
| TMPTA | 1.8 |
| $H_2O_2$/iron (initiator) | 1 |
| Poly[N-vinylformamide] | 8 |

The polymer was prepared by the solution method in water. The monomers were dissolved in water, the reaction mixture was rendered inert, and then, after initial heating, the reaction was initiated by means of a suitable redox couple. The polymer solution was subsequently evaporated down and the polymer was isolated by this means.

Chemical designation of the products employed

| | |
| --- | --- |
| TMPTA | trimethylolpropane triacrylate |
| AMA | allyl methacrylate |
| ABAH | azobisamidopropyl hydrochloride |
| AIBN | azoisobutyronitrile |

What is claimed is:

1. A water-soluble or water-swellable grafted copolymer obtained by free-radical copolymerization of
    A) 50 to 99.5 wt-% of acryloyldimethyltaurine or acryloyldimethyltaurates, and mixtures thereof, and
    B) optionally, one or more other olefinically unsaturated, comonomer containing at least one oxygen, nitrogen, sulfur or phosphorus atom and possessing a molecular weight of less than 500 g/mol, the copolymerization,
    C) taking place in the presence of at least one polymeric additive having a number-average molecular weight of from 200 g/mol to $10^9$ g/mol, prepared by precipitation polymerization in tert-butanol.

2. The water-soluble or water-swellable grafted copolymer as claimed in claim 1, further comprising one or more comonomer B).

3. The water-soluble or water-swellable grafted copolymer as claimed in claim 2, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

4. The water-soluble or water-swellable grafted copolymer of claim 1, wherein the polymeric additive C) is selected from the group consisting of a homopolymer or copolymer of a compound selected from the group consisting of N-vinylformamide, N-vinylacetamide, N-vinylpyrrolidone, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC) and/or [2-(methacryloyloxy)ethyl]trimethylammonium chloride (MAPTAC), and mixtures thereof.

5. The water-soluble or water-swellable grafted copolymer of claim 1, wherein the polymeric additive C) is selected from the group consisting of poly(N-vinylformamides), poly (N-vinylcaprolactams), and copolymers of a compound selected from the group consisting of N-vinyl-pyrrolidone, N-vinylformamide, acrylic acid, and mixtures thereof.

6. The water-soluble or water-swellable grafted copolymer of claim 1, wherein the copolymer is crosslinked.

* * * * *